United States Patent

Hauck et al.

[11] 4,065,485
[45] Dec. 27, 1977

[54] CYCLITOLAMINES

[75] Inventors: Frederic P. Hauck, Somerville; Joyce Reid, Highland Park, both of N.J.

[73] Assignee: E. R. Squibb & Sons, Inc., Princeton, N.J.

[21] Appl. No.: 735,855

[22] Filed: Oct. 26, 1976

[51] Int. Cl.$^2$ .................. C07C 121/47; C07C 69/02; A61K 31/13

[52] U.S. Cl. ................. 260/464; 260/404.5; 260/456 R; 260/456 P; 260/465 D; 424/303; 424/304; 424/311; 560/256

[58] Field of Search ............. 260/464, 465 D, 551 C, 260/488 B

[56] References Cited

U.S. PATENT DOCUMENTS

| 3,894,031 | 7/1975 | Hauck et al. | 260/490 X |
| 3,971,823 | 7/1976 | Hauck et al. | 260/490 |

Primary Examiner—Joseph Paul Brust
Attorney, Agent, or Firm—Lawrence S. Levinson; Merle J. Smith; Donald J. Barrack

[57] ABSTRACT

Compounds having the structure

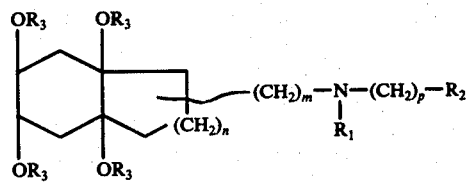

wherein $R_1$ is alkyl or arylalkyl; $R_2$ is —C≡N, —C≡CH or

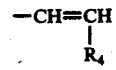

wherein $R_4$ is hydrogen, alkyl, aryl, or arylalkyl; $R_3$ is alkanoyl; $m$ is 1, 2, 3, or 4; $n$ is 1, 2, or 3; and $p$ is 0, 1, 2 or 3; are useful for the treatment of hypertension.

9 Claims, No Drawings

CYCLITOLAMINES

BACKGROUND OF THE INVENTION

U.S. Pat. No. 3,894,031, issued July 8, 1975, discloses, inter alia, that compounds having the formula

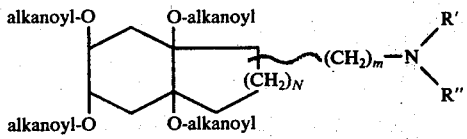

wherein R' and R" are the same or different and can be hydrogen, alkyl, haloalkyl, cycloalkyl, cycloalkylalkyl, aryl, arylalkyl, or heterocyclic, or the group —NR'R" can be a heterocyclic group, are useful for the treatment of hypertension.

U.S. Pat. No. 3,971,823, issued on July 23, 1976, discloses that compounds having the structure

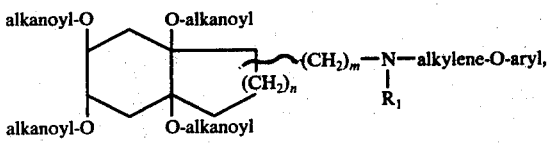

wherein $R_1$ is alkyl or arylalkyl, are useful for the treatment of hypertension.

SUMMARY OF THE INVENTION

Compounds having the formula

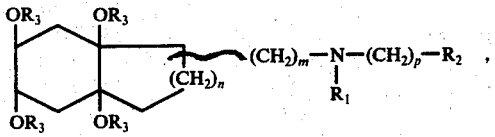

and the pharmaceutically acceptable acid-addition salts thereof, are useful for the treatment of hypertension. In formula I, and throughout the specification, the symbols are as defined below.

$R_1$ is alkyl or arylalkyl;
$R_2$ is —C≡N, —C≡CH or $$-CH=CH\atop\phantom{-}|\atop R_4$$

wherein $R_4$ is hydrogen, alkyl, aryl, or arylalkyl;
$R_3$ is alkanoyl;
$m$ is 1, 2, 3, or 4;
$n$ is 1, 2, or 3; and $p$ is 0, 1, 2, or 3.

The term "aryl", as used throughout the specification, refers to phenyl or phenyl substituted with one or two halogen, alkyl or alkoxy groups.

The terms "alkyl" and "alkoxy", as used throughout the specification, refer to groups having 1 to 6 carbon atoms.

The term "alkanoyl", as used throughout the specification, refers to groups having the formula

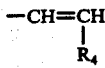

wherein Y is alkyl as defined above.

DETAILED DESCRIPTION OF THE INVENTION

The products of formula I can be prepared from compounds having the structure

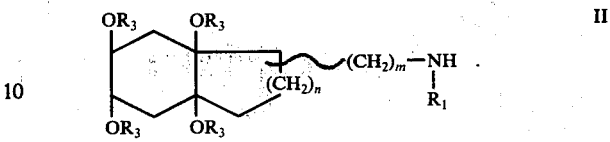

The compounds of formula II are known; see, for example, U.S. Pat. No. 3,894,031 issued July 8, 1975.

Reaction of a compound of formula II with a compound having the formula

$$X-(CH_2)_p-R_2,\qquad\text{III}$$

wherein X is chlorine or bromine, yields the corresponding compound of formula I. The reaction can be run in an organic solvent, e.g., benzene, in the presence of an organic base, e.g., triethylamine. Reaction conditions are not critical, but the reaction will most preferably be run at room temperature.

Those compounds of formula I, wherein $p$ is 2 and $R_2$ is —C≡N, are most conveniently prepared by reacting a compound of formula II with acrylonitrile. The reaction is preferably run under reflux conditions.

The compounds of formula I can be converted to their pharmaceutically acceptable acid-addition salts using methods well known in the art. Exemplary salts are hydrohalides (e.g., hydrochloride and hydrobromide), nitrate, phosphate, borate, acetate, tartrate, methanesulfonate, benzenesulfonate, toluenesulfonate and the like.

The compounds of formula I, and the pharmaceutically acceptable acid-addition salts thereof, inhibit the conversion of angiotensin I to angiotensin II. They are useful as hypotensive agents in mammals, e.g., domestic animals such as dogs, cats, etc. Daily doses of from 5 to 50 mg/kg of animal body weight, preferably about 5 to 25 mg/kg of animal body weight can be administered in single or divided doses.

The active compounds of the present invention are administered orally, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

Compounds having the structure

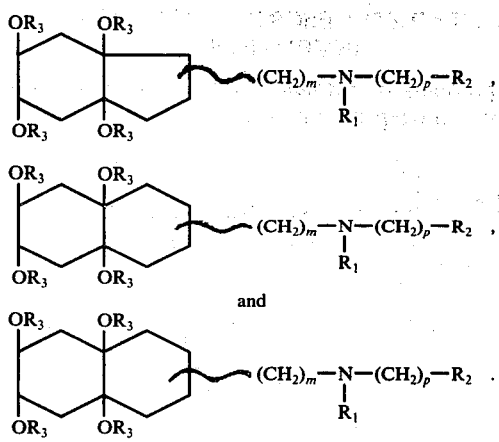

are specifically contemplated. Compounds of formulas IV, V and VI wherein $R_3$ is acetyl are preferred.

The following examples are specific embodiments of this invention.

EXAMPLE 1

3a,7a-trans-5,6-trans-1-[3-(Allylmethylamino)propoxy]-hexahydro-3a,5,6,7a-indantetrol, tetraacetate ester 3a,7a-trans-5,6-trans-Hexahydro-1-[3-(methylamino)-propyl]-3a,5,6,7a-indantetrol, tetraacetate ester (10.0 g.), triethylamine (2.6 g) and allyl bromide (3.0 g) are dissolved in 100 ml benzene and stirred at room temperature for 3 hours. The solid (6.6 g) is removed by filtration; indicating this is largely the hydobromide of the starting tetraacetate. The filtrate is washed twice with water, dried, and the solvent is removed in vacuo leaving 5.45 g of crystalline material. This is recrystallized once from benzene-hexane and once from ether-hexane to give 2.85 g of the title compound, melting point 106°–108.5° C.

EXAMPLE 2

3a,7a-trans-5,6-trans-1-[3-(Cinnamylmethylamino)-propyl]hexahydro-3a,5,6,7a-indantetrol, tetraacetate ester 3a,7a-trans-5,6-trans-Hexahydro-1-[3-(methylamino)-propyl]3a,5,6,7a-indantetrol, tetraacetate ester (8.54 g) and cinnamyl bromide (2.2 g) are dissolved in benzene (100 ml) and stirred for about 16 hours at room temperature. The crystalline hydrobromide (4.3 g) of the starting material is removed by filtration. The filtrate is washed twice with water. The benzene solution is dried, filtered and the solvent is removed in vacuo leaving 6.0 g of viscous material. Attempts to crystallize this material are not successful. The material is dissolved in ether and a solution of hydrogen chloride in isopropanol is added. The gummy hydrochloride is washed several times with ether, dissolved in water and the solution is extracted twice with ether. The aqueous layer is then basified with concentrated ammonium hydroxide and the free base is extracted into ether. After drying and removal of solvent 4.26 of foam remains. Two crystallizations from ether give 1.05 g of the title compound, melting point 96°–105° C.

EXAMPLE 3

3a,7a-trans-5,6-trans-Hexahydro-1-[3-[methyl(2-propynyl)amino]propyl]-3a,5,6,7a-indantetrol, tetraacetate ester 3a,7a-trans-5,6-trans-Hexahydro-1-[3-(methylamino)-propyl]3a,5,6,7a-indantetrol, tetraacetate ester
3a,7a-trans-5,6,-trans-Hexahydro-1-[3-(methylamino)propyl]-3a,5,6,7a-indantetrol, tetracetate ester (10.0 g), triethylamine (3.0 g) and propargyl bromide (3.0 g) are dissolved in 100 ml of benzene and the mixture is stirred for about 16 hours at room temperature. The resulting precipitate is removed by filtration. The filtrate is washed twice with water, dried, and the solvent is removed in vacuo leaving 6.85 g of partially crystalline material. This is recrystallized from ether-hexane to yield 4.85 g of the title compound, melting point 112°–120° C.

EXAMPLE 4

3-[[3-(3a,7a-trans-5,6-trans-Hexahydro-3a,5,6,7a-tetrahydroxy-1-indanyl)propyl]methylamino]propionitrile, tetraacetate ester A mixture of 3a,7a-trans-5,6-trans-Hexahydro-1-[3(methylamino)propyl]-3a,5,6,7a-indantetrol, tetraacetate ester (8.54 g) and acrylonitrile (50 ml) is heated under reflux conditions for about 16 hours in a nitrogen atmosphere. After cooling, ether is added and a small amount of insoluble material is removed by filtration. The solvent is removed in vacuo leaving 9.9 g of viscous material. Crystallization from ether gives a first crop of 3.79 g. This is recrystallized from ether-ethyl acetate to give 2.43 g of the title compound, melting point 95°–116° C.

EXAMPLES 5–13

Following the procedure of Example 3, but substituting the compound listed in column I for 3a,7a-trans-5,6-trans-hexahydro-1-[3-(methylamino)propyl]-3a,5,6,7a-indantetrol, tetraacetate ester and the compound listed in column II for allyl bromide, yields the compound listed in column III.

|   | Column I | Column II | Column III |
|---|----------|-----------|------------|
| 5 | 3a,7a-trans-5,6-trans-hexahydro-1-[(methylamino)methyl]-3a,5,6,7a-indantetrol, tetraacetate ester | 1-pentenyl bromide | 3a,7a-trans-5,6-trans-hexahydro-1-[[(1-pentenyl)methylamino]methyl]-hexahydro-3a,-5,6,7a-indantetrol, tetraacetate ester |
| 6 | 3a,7a-trans-5,6-trans-hexahydro-1-[2-(methylamino)ethyl]-3a,5,6,7a-indantetrol, tetraacetate ester | 3-butenyl bromide | 3a,7a-trans-5,6-trans-1-[2-[(3-butenyl)methylamino]-ethyl]-hexahydro-3a,5,6,7a-indantetrol, tetraacetate ester |
| 7 | 3a,7a-trans-5,6-trans-hexahydro-1-[4-(methylamino)butyl]-3a,5,6,7a-indantetrol tetraacetate ester | 3-(p-chlorophenyl)-2-propenyl chloride | 3a,7a-trans-5,6-trans-1-[4-[[3-(p-chlorophenyl)-2-propenyl]methylamino]butyl]-hexahydro-3a,5,6,7a-indantetrol, tetra-acetate ester |
| 8 | 2,3-trans-4a,8a-trans-decahydro-5-[(methylamino)methyl]-2,3,4a,8a- | 3-(p-methylphenyl)-1-propenyl chloride | 2,3-trans-4a,8a-trans-decahydro-5-[[[3-(p-methylphenyl)-1-pro- |

-continued

| | Column I | Column II | Column III |
|---|---|---|---|
| | naphthalentetrol, tetraacetate ester | | penyl]methylamino]methyl]-2,3,4a,-8a-naphthalenetetrol, tetra-acetate ester |
| 9 | 2,3-trans-4a,8a-trans-decahydro-5-[2-(methylamino)ethyl]-2,3,4a,8a-naphthalenetetrol, tetraacetate ester | 3-(p-methoxyphenyl)-1-propenyl chloride | 2,3-trans-4a,8a-trans-decahydro-5-[2-[[3-(p-methoxyphenyl)-1-propenyl]methylamino]ethyl]-2,3,4a,-8a-naphthalenetetrol, tetraacetate ester |
| 10 | 2,3-trans-4a,8a-trans-decahydro-5-[3-(methylamino)propyl]2,3,4a,8a-naphthalenetetrol, tetraacetate ester | allyl bromide | 2,3-trans-4a,8a-trans-5-[3-(allylmethylamino)propyl]-decahydro-2,3,4a,8a-naphthalenetetrol, tetraacetate ester |
| 11 | 2,3-trans-4a,9a-trans-hexahydro-7-[4-(methylamino)butyl]-2,3,4a,9a-penzocycloheptane, tetraacetate ester | cinnamyl chloride | 2,3-trans-4a,9a-trans-7-[4-(cinnamylmethylamino)butyl]-2,3,4a,9a-hexahydro-benzocyclo-, heptane, tetraacetate ester |
| 12 | 2,3-trans-4a,9a-trans-hexahydro-7-8 3-(isopropylamino)propyl]-2,3,4a,9a-penzocycloheptane, tetraacetate ester | 2-butenyl bromide | 2,3-trans-4a,9a-trans-7-[3-[(2-butenyl)isopropylamino]-propyl]-hexahydro-2,3,4a,9a-benzocycloheptane, tetraacetate ester |
| 13 | 2,3-trans-4a,8a-trans-decahydro-5-[3-(methylamino)propyl]-2,3,4a,8a-naphthalenetetrol, tetraacetate ester | 4-pentenyl bromide | 2,3-trans-4a,8a-trans-decahydro-5-[3-[(4-pentenyl)methylamino]-propyl]-2,3,4a,8a-naphthalenetetrol, tetraacetate ester |

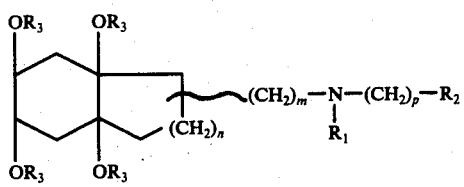

EXAMPLES 14–17

Following the procedure of example 3, but substituting the compound listed in column I for 3a,7a-trans-5,6-trans-hexahydro-1-[3-(methylamino)propyl]-3a,5,6,7a-indantetrol, tetra-acetate ester and the compound listed in column II for propargyl bromide, yields the compound listed in column III.

| | Column I | Column II | Column III |
|---|---|---|---|
| 14 | 3a,7a-trans-5,6-trans-hexahydro-1-[(methylamino)methyl]-3a,5,6,7a-indantetrol, tetraacetate ester | ethynyl bromide | 3a,7a-trans-5,6-trans-hexahydro-1-[(ethynylmethylamino)melthyl]-3a,5,6,7a-indantetrol, tetra-acetate ester |
| 15 | 3a,7a-trans-5,6-trans-hexahydro-1-[2-(methylamino)ethyl]-3a,5,6,7a-indantetrol, tetraacetate ester | 3-butynyl bromide | 3a,7a-trans-5,6-trans-1-[2-[(3-butynyl)methylamino]ethyl]-hexahydro-3a,5,6,7a-indantetrol, tetra-acetate ester |
| 16 | 2,3-trans-4a,8a-trans-decahydro-5-[3-(methylamino)propyl]-2,3,4a,8a-haphthalenetetrol, tetraacetate ester | 4-pentynyl bromide | 2,3-trans-4a,8a-trans-decahydro-1-[3-[methyl(4-pentynyl)amino]propyl]-2,3,4a,8a-naphthalenetetrol |
| 17 | 2,3-trans-4a,9a-trans-hexahydro-7-[4-(methylamino)butyl]-2,3,4a,9a-benzocycloheptane, tetraacetate ester | ethynyl bromide | 2,3-trans-4a,9a-trans-7-[4-(ethynylmethylamino)butyl]-hexahydro-2,3,4a,9a-benzocycloheptane, tetraacetate ester |

EXAMPLES 18–19

Following the procedure of example 4, but substituting the compound listed in column I for 3a,7a-trans-5,6-trans-hexahydro-1- [3-(methylamino)propyl]-3a,5,6,7a-indantetrol, tetraacetate ester, yields the compound listed in column II.

| | Column I | Column II |
|---|---|---|
| 18 | 2,3-trans-4a,8a-trans-decahydro-5[3-(methylamino)propyl]-2,3,-4a,8a-naphthalenetetrol, tetra-acetate ester tetraacetate ester | 3-[[3-(2,3-trans-4a,8a-trans-decahydro-2,3,4a,8a-tetra-hydroxy-5-naphthyl)propyl]-methylamino]propionitrile, |
| 19 | 2,3-trans-4a,9a-trans-hexahydro- | 3-[[3-(2,3-trans-4a,9a-trans- |

-continued

| | Column I | Column II |
|---|---|---|
| | 7[3-(methylamino)propyl]-2,3,-4a,9a-benzocycloheptane, tetra-acetate ester | hexahydro-2,3,4a,9a-tetra-hydroxy-7-benzocyclohep-tyl)-propyl]methylamino]pro-pioni-trile, tetraacetate ester |

What is claimed is:
1. A compound having the formula

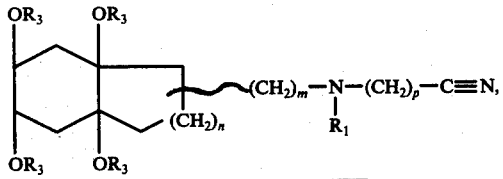

or a pharmaceutically acceptable acid-addition salt thereof, wherein $R_1$ is alkyl or arylalkyl; $R_3$ is alkanoyl of 1 to 7 carbon atoms; $m$ is 1, 2, 3 or 4; $n$ is 1, 2 or 3; and $p$ is 0, 1, 2 or 3; wherein aryl is phenyl or phenyl substituted with one or two halogen, alkyl or alkoxy groups; and alkyl and alkoxy are groups having 1 to 6 carbon atoms.

2. A compound in accordance with claim 1 wherein $n$ is 1.

3. A compound in accordance with claim 1 wherein $n$ is 2.

4. A compound in accordance with claim 1 wherein $n$ is 3.

5. A compound in accordance with claim 1 wherein $R_1$ is alkyl.

6. A compound in accordance with claim 5 wherein $R_1$ is methyl.

7. A compound in accordance with claim 1 wherein $R_3$ is acetyl.

8. A compound in accordance with claim 1 wherein $m$ and $p$ are the same or different and are 2 or 3.

9. A compound in accordance with claim 1 wherein $R_1$ is methyl, $R_3$ is acetyl, and $m$ and $p$ are the same or different and are 2 or 3.

* * * * *

UNITED STATES PATENT AND TRADEMARK OFFICE
CERTIFICATE OF CORRECTION

PATENT NO. : 4,065,485
DATED : December 27, 1977
INVENTOR(S) : Frederic P. Hauck et al.

It is certified that error appears in the above-identified patent and that said Letters Patent are hereby corrected as shown below:

Column 3, line 33, - "hydobromide" should read
-- hydrobromide --.
Column 4, Example 3, please omit lines 17 and 18
as they are repetitious of lines 19 and 20.
Example 7, Column III, please correct the last line to
read -- 3a,5,6,7a-indanetetrol, tetraacetate ester --.
Example 8, Column II, please remove "acetate ester".
Example 12, Column I, in line 1 "7-8 3'" should read
-- 7-[3- --, and in line 3 "penzocycloheptane"
should read -- benzocycloheptane --.
Example 14, Column I, please remove "acetate ester" (last line).
Example 14, Column III, please correct the last line to read
-- 3a,5,6,7a-indantetrol,  tetraacetate ester --.
Example 18, Column I, please remove "tetraacetate ester",
(second occurrence).
Example 18, Column II, please add -- tetraacetate ester --
as the last line.

Signed and Sealed this

Twenty-third Day of May 1978

[SEAL]

Attest:

RUTH C. MASON
Attesting Officer

LUTRELLE F. PARKER
Acting Commissioner of Patents and Trademarks